United States Patent [19]

Dockner et al.

[11] Patent Number: 4,550,176

[45] Date of Patent: Oct. 29, 1985

[54] PREPARATION OF IMIDAZOLE-4,5-DICARBOXYLIC ACID

[75] Inventors: Toni Dockner, Meckenheim; Uwe Kempe, Dannstadt-Schauernheim; Anton Frank, Ludwigshafen, all of Fed. Rep. of Germany

[73] Assignee: BASF Aktiengesellschaft, Ludwigshafen, Fed. Rep. of Germany

[21] Appl. No.: 569,965

[22] Filed: Jan. 11, 1984

[30] Foreign Application Priority Data

Jan. 20, 1983 [DE] Fed. Rep. of Germany ....... 3301717

[51] Int. Cl.$^4$ ............................................. C07D 233/90
[52] U.S. Cl. .................................... 548/343; 548/342
[58] Field of Search ................................. 548/342, 343

[56] References Cited

PUBLICATIONS

Godefroi, E. et al., *Rec. Trav. Chim.*, 91, 1383–1392 (1972).

Masui, M. et al., *Chem. Pharm. Bull.* (Japan), 22 (10), 2359–2364 (1974).

Hubball, W. et al., *J. Chem. Soc.*, 28 (1928).

*Primary Examiner*—Richard A. Schwartz
*Attorney, Agent, or Firm*—John H. Shurtleff

[57] ABSTRACT

Imidazole-4,5-dicarboxylic acid is prepared by a process in which imidazole is reacted with formaldehyde, and the reaction mixture is treated with nitric acid.

15 Claims, No Drawings

PREPARATION OF IMIDAZOLE-4,5-DICARBOXYLIC ACID

Imidazole-4,5-dicarboxylic acid is a useful intermediate for drugs. For example, the amides which can be readily obtained from this acid have a stimulating effect on the central nervous system, and are also used therapeutically as sedatives. Imidazole-4,5-dicarboxylic acid is also used for the preparation of 4-aminoimidazole-5-carboxylic acid, an intermediate for purine syntheses, and is furthermore an important building block for semi-synthetic penicillins and cephalosporins with excellent activity.

Imidazole-4,5-dicarboxylic acid can be prepared, for example, by reacting tartaric acid dinitrate with ammonia and formaldehyde in aqueous solution (Ann. Chem. Phys. 24 (1891), 523–525). This acid can also be obtained by oxidation of benzimidazole with potassium dichromate or potassium permanganate (Z. obsc. Chem. 26 (1956), 455).

These processes have the disadvantage that they require expensive starting materials.

It is an object of the present invention to provide a synthesis which permits the preparation of this desirable intermediate by an economical route.

We have found that this object is achieved, and that imidazole-4,5-dicarboxylic acid can be particularly advatageously prepared, if imidazole is reacted with a 2-fold to 5-fold molar amount of formaldehyde at elevated temperatures, and the reaction mixture is treated with nitric acid at from 100° to 140° C.

This novel process is particularly economical owing to the cheap starting materials used, and makes it possible to obtain imidazole-4,5-dicarboxylic acid in a simple manner and in good yields.

The process according to the invention can be represented by the following equation:

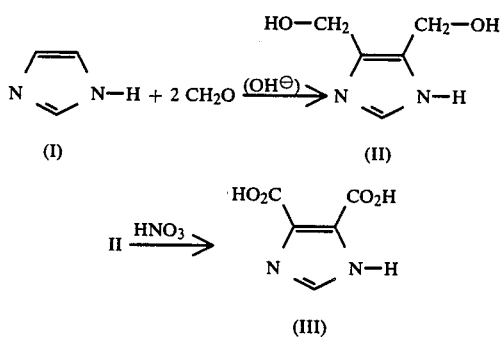

The compound (II) is a mixture of imidazole derivatives having various degrees of hydroxymethylation. According to HPLC analysis, the reaction mixture contains 4,5-bishydroxymethylimidazole and 1,2,4,5-tetrahydroxymethylimidazole, in addition to small amounts of 1-hydroxymethylimidazole and 4-hydroxymethylimidazole. It also contains oligomeric condensates which undergo secondary reactions under the reaction conditions, as hydroxymethyl compounds are known to do.

In the novel process, imidazole is reacted with a 2-fold to 5-fold, preferably 2.5-fold to 3.5-fold, molar amount of formaldehyde at elevated temperatures, preferably at from 80° to 120° C. It is also possible to use paraformaldehyde instead of formaldehyde. Advantageously, the reaction is carried out in aqueous solution, and the formaldehyde is used in the form of the commercial 30–40% strength aqueous solution. Advantageously, this reaction is carried out in the presence of a strong base, such as an alkali metal or alkaline earth metal hydroxide, preferably KOH or NaOH. The base is used in general in an amount of from 30 to 100, preferably from 45 to 55, mole %, based on the imidazole. The reaction time is about 1–3 hours. The first stage of the reaction can be monitored, for example by HPLC.

The reaction mixture obtained from this reaction is then treated, either directly or after being concentrated, with nitric acid at from 100° to 140° C., preferably from 130° to 135° C. This stage of the process, too, is preferably carried out in aqueous solution. The molar ratio of nitric acid to imidazole is advantageously from 15:1 to 20:1, and the reaction time is about 6–10 hours. The procedure is, for example, as follows: 65% strength nitric acid is initially taken in a stirred flask and heated at the boil, and an aqueous solution of the oligohydroxymethylimidazoles is slowly added to the boiling acid. During the reaction, water is distilled off and the aqueous reaction mixture is concentrated. When the reaction is complete, the mixture is cooled, and a pure imidazole-4,5-dicarboxylic acid crystallizes out. The acid is filtered off, washed with water and dried. A second fraction of imidazole-4,5-dicarboxylic acid can be obtained from the filtrate by bringing the pH to 4. The filtrate can be replenished with fresh nitric acid and then reused for the process.

EXAMPLE 1

68 g of imidazole are dissolved in 245 g of a 37% strength by weight aqueous formaldehyde solution, 28 g of potassium hydroxide are added to the solution, and the mixture is refluxed for 3 hours. 1.3 liters of 65% strength nitric acid are heated at the boil in a stirred flask equipped with a 50 cm column having a reflux divider, a contact thermometer and a dropping funnel. The reaction mixture containing the oligohydroxymethylimidazole compounds is then added dropwise to the boiling nitric acid in the course of 1 hour, and the mixture boils under reflux with vigorous evolution of nitrous gases. 30 minutes after the dropwise addition is complete, the evolution of these gases ceases. About 500 g of a 5–8% strength nitric acid are distilled off in the course of from 5 to 6 hours at from 100° to 102° C. and with a reflux ratio of 10:1. The reaction mixture is cooled in an ice bath, and the precipitated crystals are filtered off under suction, washed with 150 ml of water and dried. 50 g of imidazole-4,5-dicarboxylic acid having a purity of 96.6% (according to HPLC) and a melting point of 287°–289° C. (decomposition) are obtained. The filtrate is cooled with ammonia water and thus neutralized, and is brought to pH 4 with formic acid. A further 76 g of 95.2% pure imidazole-4,5-dicarboxylic acid crystallizes out. The total yield is 120 g of imidazole-4,5-dicarboxylic acid, corresponding to 77.0% of theory.

EXAMPLE 2

The procedure described in Example 1 is followed, except that, after 68 g of imidazole-4,5-dicarboxylic acid have been isolated, the filtrate containing nitric acid is not neutralized but is made up to 1.3 liters with fresh 65% strength nitric acid, and heated at the boil in the distillation apparatus. When the evolution of nitrous gases is complete, the starting mixture prepared as described in Example 1, and containing the oligohydroxymethylimidazole compounds, is added dropwise as described in Example 1. The resulting water of reaction is then distilled off in the form of about 5–8% strength nitric acid, and the imidazole-4,5-dicarboxylic acid formed is isolated as described above. This procedure can be repeated as often as desired. The resulting potassium nitrate is removed by washing the crystalline imidazole-4,5-dicarboxylic acid.

The yields of imidazole-4,5-dicarboxylic acid are from 75 to 80%, based on the imidazole employed.

We claim:

1. A process for the preparation of imidazole-4,5-dicarboxylic acid which comprises:
   reacting imidazole in a first stage with a 2-fold to 5-fold molar amount of formaldehyde at elevated temperatures, and then treating the reaction mixture in a second stage with nitric acid at from 100° to 140° C.

2. A process as claimed in claim 1, wherein the reaction of imidazole with formaldehyde is carried out in the presence of a strong base.

3. A process as claimed in claim 1, wherein the reaction of imidazole with formaldehyde is carried out in aqueous solution.

4. A process as claimed in claim 1, wherein the reaction of imidazole with formaldehyde is carried out at from 80° to 120° C.

5. A process as claimed in claim 2, wherein the strong base used is an alkali metal or alkaline earth metal hydroxide.

6. A process as claimed in claim 1, wherein the molar ratio of nitric acid to imidazole is from 15:1 to 20:1.

7. A process as claimed in claim 1, wherein the first stage reaction of imidazole is carried out in an aqueous solution in the presence of a strong base and at an elevated temperature of from 80° to 120° C.

8. A process as claimed in claim 7 wherein the strong base is used in an amount of from 30 to 100 mole% based on the imidazole.

9. A process as claimed in claim 8 wherein the strong base is an alkali metal or alkaline earth metal hydroxide.

10. A process as claimed in claim 7 wherein the second stage treatment is carried out in aqueous solution with a molar ratio of nitric acid to imidazole of from 15:1 to 20:1.

11. A process as claimed in claim 10, wherein the second stage treatment is carried out at a temperature of from 130° to 135° C.

12. A process as claimed in claim 10 wherein the strong base used in the first stage is an alkali metal or alkaline earth metal hydroxide.

13. A process as claimed in claim 12 wherein the strong base is selected from the group consisting of KOH and NaOH.

14. A process as claimed in claim 1, wherein the reaction mixture obtained after treatment in said second stage is cooled, and the imidazole-4,5-dicarboxylic acid product is crystallized out and separated.

15. A process as claimed in claim 14 wherein the first stage reaction time is about 1 to 3 hours, and the second stage reaction time is about 6 to 10 hours.

* * * * *